US008143317B2

(12) United States Patent
Petzelt et al.

(10) Patent No.: US 8,143,317 B2
(45) Date of Patent: *Mar. 27, 2012

(54) USE OF XENON FOR TREATING NEUROINTOXICATIONS

(75) Inventors: Christian Petzelt, Berlin (DE); Wolfgang J. Kox, Bergheim (DE)

(73) Assignee: Air Products and Chemicals, Inc., Allentown, PA (US)

(*) Notice: Subject to any disclaimer, the term of this patent is extended or adjusted under 35 U.S.C. 154(b) by 612 days.

This patent is subject to a terminal disclaimer.

(21) Appl. No.: 11/650,211

(22) Filed: Jan. 4, 2007

(65) Prior Publication Data

US 2007/0110821 A1    May 17, 2007

Related U.S. Application Data

(60) Continuation of application No. 10/342,968, filed on Jan. 15, 2003, now abandoned, which is a division of application No. 09/936,319, filed as application No. PCT/EP00/02025 on Mar. 8, 2000, now Pat. No. 6,559,190.

(30) Foreign Application Priority Data

Mar. 11, 1999  (DE) ................................ 199 10 986

(51) Int. Cl.
*A01N 25/00* (2006.01)
*A61K 47/00* (2006.01)
*A61K 51/00* (2006.01)
*A61M 36/14* (2006.01)

(52) U.S. Cl. ...................................... 514/771; 424/1.18
(58) Field of Classification Search .................... 514/771
See application file for complete search history.

(56) References Cited

U.S. PATENT DOCUMENTS

| 5,228,434 | A | | 7/1993 | Fishman |
| 5,357,959 | A | * | 10/1994 | Fishman ...................... 600/420 |
| 6,274,633 | B1 | | 8/2001 | Franks et al. |

FOREIGN PATENT DOCUMENTS

| DE | 197 09 704 A1 | 9/1998 |
| EP | 864 328 A1 | 9/1998 |
| EP | 864 329 B1 | 12/2000 |

OTHER PUBLICATIONS

Radue et al. (Xenon Enhancement in Tumours and Infarcts, Neuroradiology 16, 224-227, 1978.*
Luttropp et al.( Clinical experience with minimal flow xenon anesthesia vol. 38 Issue 2, pp. 121-125).*
Sagratella, "NMDA Antagonists: Antiepileptic-Neuroprotective Drugs with Diversified Neuropharmacological Profiles." Pharmacological Research (1995), vol. 32, No. 1/2, pp. 1-13.
Hudspith, "Glutamate: a Role in Normal Brain Function, Anaesthesia, Analgesia and CNS Injury." British Journal of Anaesthesia (1997), 78: 731-747.
Jevtovic-Todorovic, "Nitrous Oxide (Laughing Gas) is an NMDA Antagonist, Neuroprotectant and Neurotoxin." Nature Medicine, vol. 4, No. 4, Apr. 1998, pp. 460-463.
Wiegt, et al. "Xenon Inhibits AMPA- and Kainate-Induced Membrane Currents in Cortical Neurons." Anesthesiology, vol. 101, Oct. 26, 2004, A-870.
Abraini, "Neurodegenerescence: Modeles et Strategies Therapeutiques." Centre National de la Recherche Scientifique, May 23, 2005.
Parsons, et al. "Glutamate in CNS Disorders as a Target for Drug Development: An Update." Drug News & Perspectives, vol. 11, No. 9, Nov. 1998, pp. 523-569.
Hill, "Tissue Culture—PC12 Cells." UNSW Faculty of Medicine, School of Anatomy.
Hacke, "Neuroprotection as Initial Therapy in Acute Stroke." Cerebrovascular Diseases (1998), 8:59-72.
Wahlgren, "A Review of Earlier Clinical Studies on Neuroprotective Agents and Current Approaches." Neuroprotective Agents and Cerebral Ischaemia (1997), pp. 337-363.
Jain, "Neuroprotection: Drugs, Companies and Markets." Oct. 2004.
Franks et al., "How does xenon produce anaesthesia?", Nature, vol. 396, p. 324, Nov. 1998.
Beckers, J.M., and Stevens, C.F., Proc. Natl. Acad. Sci. USA 88: 7834-7838 (1991).
Brockmeyer, D.M., and Kendig, J.J., Br. J. Anaesthesia 74: 79-84 (1995).
Cullen, S.C., et al., Anesthesiology 31: 305-309 (1969).
Cullen, S.C., and Gross, E.G., Science 113:580-582 (1951).
Davies, J., et al., Neurosci. Lett. 21: 77-81 (1981).
Franks, N.P., and Lieb, W.R., Br. J. Anaesthesia 71: 65-76 (1993).
Franks, N.P., and Lieb, W.R., Nature 367: 607-614 (1994).
Franks, N.P., and Lieb, W.R., Anesthesiology 84: 716-720 (1996).
Goto, T., et al., Anesthesiology 86: 1273-1278 (1997).
Hadingham, K.L., et al., Proc. Natl. Acad. Sci. USA 89: 6378-6382 (1997).
Kennedy, R.R., et al., Anaesth. Intens. Care 20: 66-70 (1992).
Koblin, D.D., et al., Anesth. Anal. 87: 419-424 (1998).
Lachmann, B., et al., Lancet 335: 1413-1415 (1990).
Lawrence, J.H., et al., J. Physiol. 105: 197-204 (1946).
Luttropp, H.H., et al., Acta Anaesthesiol. Scand. 38: 121-125 (1994).
Mennerick, S., et al., J. Neurophysiology 73: 320-332 (1995).

(Continued)

*Primary Examiner* — Sreeni Padmanabhan
*Assistant Examiner* — Layla Soroush
(74) *Attorney, Agent, or Firm* — Kenyon & Kenyon LLP

(57) ABSTRACT

Methods for treating mammals for neurointoxication are provided comprising treating the mammal with a xenon-containing gas. Methods of providing neuroprotection in mammals are also disclosed comprising administering therapeutically effective amounts of xenon, preferably in combination with pharmaceutically acceptable carriers, diluents or excipients.

11 Claims, 2 Drawing Sheets

OTHER PUBLICATIONS

Mihic, S.J., et al., Nature 389: 385-389 (1997).
Segal, M.M., and Furshpan, E.J., J. Neurophysiology 64: 1390-1399 (1990).
Smith, R.A., et al., Biochim. Biophys. Acta 645: 327-338 (1981).
Tanelian, D.L., et al., Anesthesiology 78: 757-776 (1993).
Watkins, J.C., and Evans, R.H., Ann. Rev. Pharmacol. Toxicol. 21: 165-204 (1981).
Weathersby, P.K., and Homer, L.D., Undersea Biomedical Res. 7: 277-296 (1980).
Whitehurst, S.L., J. Neurosurgical Anesthesiology 6: 275-279 (1994).
Wlaz, P., et al., Eur. J. Neuroscience 6: 1710-1719 (1994).
Kumar, G.K., et al., AJP: Cell, 274 (6), C1592-1600 (Jun. 1988).
Clemens, J.A, and Phebus, L.A., Life Sciences, vol. 42, pp. 707-713 (1987).
Kahn, R.A., et al., Anesth. Analg. 1955; 80:1116-21.
Georgieff, M., et al., (4) Deutsches Arzteblatt 94, Heft 34-35, Aug. 25, 1997, pp. A-2202-A-2205.
Kondoh, T., et al., Neurosurgery, vol. 35, No. 2, Aug. 1994, pp. 278-286.
Werling, L.L., et al., Brain Research, 606 (1993) 99-105.
McLaughlin, B.A., et al., Journal of Neurochemistry, pp. 2406-24-15 (1997).

* cited by examiner

USE OF XENON FOR TREATING NEUROINTOXICATIONS

CROSS-REFERENCE TO RELATED APPLICATIONS

This is a divisional of U.S. patent application Ser. No. 09/936,319, filed on Dec. 19, 2001.

FIELD OF THE INVENTION

The present invention relates to the use of xenon for treating neurointoxications. More particularly, the present invention relates to a use of xenon in which the neurointoxication is caused by a neurotransmitter excess.

BACKGROUND OF THE INVENTION

The uncontrolled release of neurotransmitters, particularly glutamate, noradrenalin and dopamine, is responsible for many acute and chronic intoxications of the brain. These are called neurointoxications or neuropoisonings. These neurotransmitters kill the affected neurons either by induction of apoptosis (controlled cell death) and/or secondarily by their metabolites, by forming oxygen radicals which in turn have toxic effects. An uncontrolled release of neurotransmitters which result in a strongly increased concentration of the neurotoxins in the affected tissue, can be due to various endogenous or exogenous causes. For example, an increased release of glutamate or dopamine may result in an acute craniocerebral trauma. An increase in the neurotransmitter release has also been observed as a response to oxygen deficiency in the brain, e.g. in the case of apoplexy (ischemia) or in the case of other hypoxias, particularly during childbirth. Drug abuse represents another cause of impaired neurotransmitter release. In certain forms of schizophrenia, stress-induced relapses back into schizophrenia (acute episodes) are also accompanied by increased neurotransmitter release. Finally, a chronic shift of neurotransmitter balance, particularly of dopamine balance, has also been observed in various regions of the brain in the case of Parkinson's disease. Increased dopamine release and subsequent formation of free radicals occur in that case as well. Various investigations made with cell cultures and experimental animals have proven the release of neurotransmitters, particularly as a result of oxygen deficiency.

For example, it can be shown that in rats into which the dopamine neurotoxin 6-hydroxy-dopamine was infused unilaterally into the *substantia nigra*, which resulted in a unilateral depletion of dopamine in the ipsilateral striatum, an experimentally induced ischemia in the regions of dopamine depletion led to damage which was less than that in other regions of the brain. These results suggest that dopamine plays a part in ischemia-induced striatal cell death (Clemens and Phebus, Life Science, Vol. 42, p. 707 et seq., 1988).

It can also be shown that dopamine is released in great amounts from the striatum during cerebral ischemia (Kahn et al., Anest.-Analg., Vol. 80, p. 1116 et seq., 1995).

The release of neurotransmitters during cerebral ischemia was investigated in detail and seems to play a key role for excitotoxic neural death. For example, Kondoh et al., Neurosurgery, Vol. 35, p. 278 et seq., 1994, showed that changes in the neurotransmitter release and metabolization can reflect changes in the cellular metabolism during ischemia. The increase in the extracellular dopamine concentration in the striatum of experimental animals in which experimental apoplexies were induced, is well documented.

The contribution of excess dopamine to neuronal damage can be derived from the ability of dopamine antagonists to obtain protection of the neurons in ischemia models (Werling et al., Brain Research, Vol. 606, p. 99 et seq., 1993). In a cell culture, dopamine primarily causes apoptosis of striatal neurons, without damaging the cells by a negative effect on the oxidative phosphorylation the (ATP/ADP ratio remains unchanged). However, if its effect is combined with a minimum inhibition of mitochondrial functions, the neurotoxic effect of dopamine will be increased significantly (McLaughlin et al., Journal of Neurochemistry, Vol. 70, p. 2406 et seq., 1998).

In addition to the direct hypoxic toxicity on neurons, the stress induced by oxygen deficiency, particularly during a birth, effects an increased dopamine release, which results in a negative conditioning of the brain for dopaminergic regulations. This means that even children who seem to survive a hypoxic birth phase uninjured, have a tendency towards convulsions and epileptic conditions when they are older.

Another cause of a disturbed neurotransmitter release is represented by drug abuse. In particular, if drugs such as designer drugs (e.g. ecstasy, etc.) or heroin are consumed, and amphetamines are overdosed, the persons will show signs of intoxication and often spasmophilia, which is based on an increased neurotransmitter release.

The causes of schizophrenia are also due to a complex impairment of the neurotransmitter regulation. Schizophrenia patients are often asymptomatic over a prolonged period of time, but they have a tendency towards spontaneous schizophrenia attacks which are obviously triggered by a stress-induced dopamine release, even in minor stress situations. Here, one speaks of catatonic schizophrenia. Further neuropsychiatric diseases which are based on an increased neurotransmitter release are depressions and Gilles de la Tourette syndrome ("maladie de tics", "Tics impulsif").

Finally, one cause of Parkinson's disease is presently believed to be in dopamine modulation and in dopamine metabolism. In Parkinson's disease, dopaminergic neurons in the striatum are especially damaged. References exist to the effect that Parkinson's disease is caused by a dopamine excess in the affected region of the posterolateral hypothalamus and the *substantia nigra*. Many neurons which have lost their functionality but not their vitality are found in this region. These neurons, referred to as "orphan neurons," continuously release neurotransmitter amounts having pathologic effects.

With the exception of Parkinson's disease, where dopa precursors are used as preparations, basically of schizophrenia, no therapeutic approaches presently exist which focus on a reduction of the dopamine concentration in the environment of endangered cells.

Therefore, there is a demand for a preparation which reduces or prevents the damaging effects of uncontrolled neurotransmitter release, e.g. of dopamine, glutamate or noradrenalin, from neurons. It is therefore an object of the present invention to provide such a preparation which can be of use in the above-mentioned, as well as in other fields of application.

SUMMARY OF THE INVENTION

In accordance with the present invention, these and other objects have now been realized by the discovery of a method for treating a mammal for neurointoxication comprising treating the mammal with a xenon-containing gas. Preferably, the xenon-containing gas comprises a mixture of gases.

In accordance with one embodiment of the method of the present invention, the neurointoxication is caused by an excess of neurotransmitter in the mammal.

In accordance with another embodiment of the method of the present invention, treating of the mammal with the xenon-containing gas comprises reducing the release of neurotransmitters in the mammal. Preferably, the neurotransmitters are dopamine, glutamate and/or noradrenalin.

In accordance with another embodiment of the method of the present invention, the neurointoxication is caused by apoplexy. In other embodiments, the neurointoxication is caused by drug abuse, oxygen deficiency during birth, a craniocerebral trauma, loss of hearing, or migraine.

In accordance with another embodiment of the method of the present invention, the neurointoxication is correlated with a condition such as Parkinson's disease, schizophrenia, or Gilles de la Tourette syndrome.

In accordance with another embodiment of the method of the present invention, the treating of the mammal with the xenon-containing gas comprises using a cardio-pulmonary bypass machine.

In accordance with another embodiment of the method of the present invention, the xenon-containing gas comprises an administered preparation containing from 5 to 90% by volume of the xenon.

In accordance with another embodiment of the method of the present invention, the xenon-containing gas comprises an administered preparation containing from 5 to 30% by volume of the xenon.

In accordance with another embodiment of the method of the present invention, the xenon-containing gas comprises an administered preparation containing a gas such as oxygen, nitrogen or air. Preferably, the xenon-containing gas comprises oxygen, and the ratio of the xenon to the oxygen is from about 80 to 20% by volume.

In accordance with another aspect of the present invention, a treatment method has been discovered comprising using xenon as a neuroprotectant.

In accordance with yet another aspect of the present invention, a method of providing neuroprotection in a mammal has been discovered, the method comprising administering to the mammal a therapeutically effective amount of xenon. Preferably, the method includes administering the xenon in combination with a compound such as a pharmaceutically acceptable carrier, diluent and/or excipient.

In accordance with another embodiment of this method of the present invention, the method includes treating the mammal for a condition associated with NMDA receptor activity.

In accordance with another embodiment of this method of the present invention, the method includes treating the mammal for a condition associated with NMDA receptor activation.

In accordance with another embodiment of this method of the present invention, the xenon reduces the level of activation of the NMDA receptor.

In accordance with yet another aspect of the present invention, a process has been provided for the preparation of a pharmaceutical composition suitable for neuroprotection, the process comprising adding xenon to a component such as a pharmaceutically acceptable carrier, excipient and/or diluent, and using the xenon as a neuroprotectant.

In accordance with the present invention, it has been found that the noble gas xenon surprisingly now reversibly suppresses the release of neurotransmitters, particularly dopamine and glutamate. This unexpected discovery has thus created the possibility of producing preparations for treating cell damage and diseases, respectively, which are caused by an increased neurotransmitter release, and particularly dopamine release or glutamate release.

Correspondingly, the present invention generally relates to the use of xenon for treating neurointoxications, and on the production of a preparation containing xenon for treating neurointoxications, respectively. The present invention also relates to the preparations per se and to a method of producing same. Such neurointoxications particularly concern an excess of neurotransmitter. The present invention is particularly based on the insight that xenon reduces the release of dopamine and/or glutamate.

BRIEF DESCRIPTION OF THE DRAWINGS

The present invention may be more fully appreciated with reference to the following detailed description, which, in turn, refers to the Figures wherein.

DETAILED DESCRIPTION

Figure 1A:
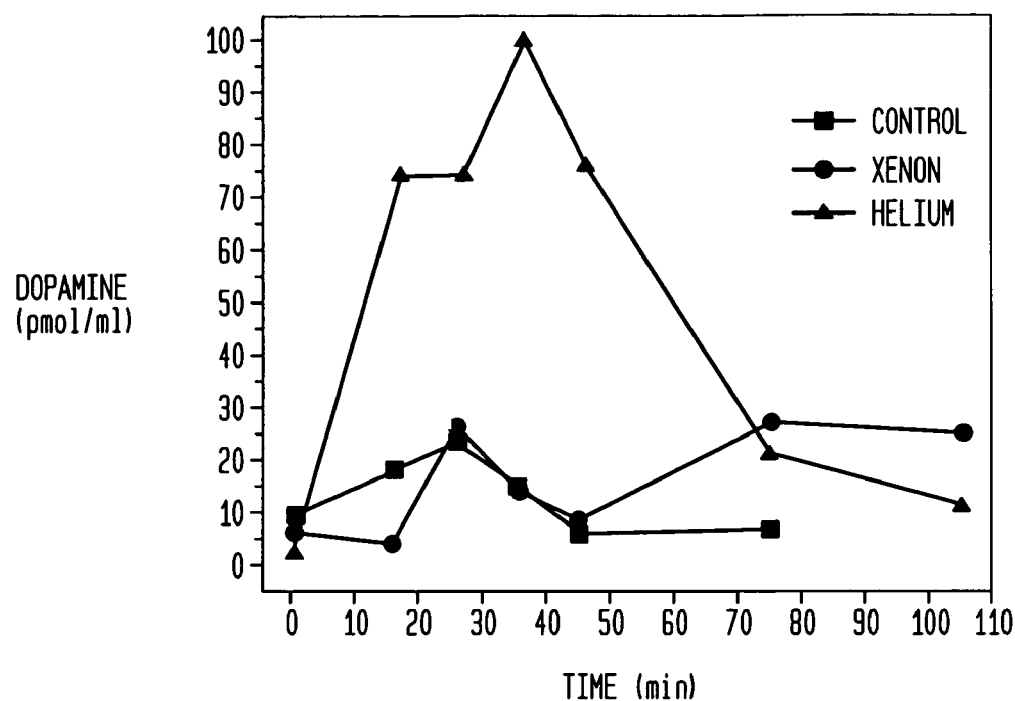
FIG. 1A is a graphical representation of the release of dopamine under various hypoxic situations.

According to the present invention neurointoxications are understood to mean acute or chronic "states of poisoning" of the central nervous system (CNS), and particularly of the brain, which in most cases result in severe deficiency symptoms of the affected areas. These states of poisoning result from an excess of neurotransmitter, particularly of glutamate, noradrenalin and/or dopamine, which can be due to a variety of causes. The above-mentioned diseases, such as apoplexy, hypoxias, oxygen deficiency during a birth, Parkinson's disease, craniocerebral trauma, drug abuse, schizophrenia, depressions and Gilles de la Tourette syndrome are among those that can be mentioned here. The inventors have also found that patients who must be connected to a cardio-pulmonary bypass machine often suffer from cerebral deficiency symptoms which are due to an excess of neurotransmitter caused by hypoxia. For example, the use of a cardio-pulmonary bypass machine can cause an often unidentified neurointoxication, which delays the patient's reconvalecence to a considerable extent. It has also been found that any prolonged artificial respiration can result in undesired neurointoxication as a side-effect. In recent investigations conducted by the inventors, the surprising insight has been gained that the hearing loss (e.g. due to noise, presbycusis, tinnitus, or sudden deafness) can also be caused by neurointoxication. The excess neurotransmitter release, particularly excessive glutamate and dopamine release, which can have been caused e.g. by an impairment in the body, an acoustic trauma, or an ischemia, results in an acute destruction of the nerve endings and subsequently death of the corresponding nerves in the hearing organs. Migraine has to be considered another disease which is most likely due to an impaired dopamine balance, and thus to neurointoxication.

The discovery that the neurotransmitter release can be influenced by xenon enables an entirely new field of application for this noble gas, which has up to now been used increasingly as an inhalation anesthetic agent in the field of anesthetics. The treatment of the differing neurotransmitter excess diseases of the brain, such as those discussed above, can be carried out on the basis of the present invention by a simple inhalation therapy. The uptake of xenon by means of the respiratory system, and transport into the brain, are already proved by its use as anesthetic agent. It can also be assumed that the use of xenon has no damaging effect on the human organism, since many corresponding experiences can be realized by its use as an anesthetic agent. Xenon can be applied by various techniques, which can be chosen as a function of the location of use. For example, inhaling apparatus can be used in the clinics, which are also used for anesthesia by inhalation. If a cardio-pulmonary bypass machine or other artificial breathing apparatus is used, xenon can be added directly in the machine, and thus requires no further apparatus. In this case, standard xenon addition can prevent the formation of neurointoxications in the model case (prophylaxis) or at least reduce the deficiency symptoms. On an ambulant basis, e.g. in the primary treatment of victims of an accident, it is possible to use simpler inhalators which mix the xenon with the ambient air during the process of inhalation. In this connection, it is also possible to adapt the xenon concentration and the timing of xenon use, a in simple manner, to the therapeutic requirements. For example, it is advantageous to use mixtures of xenon with other gases, it being possible to mix the xenon with oxygen, nitrogen, air or other gases which are harmless for humans.

In patients suffering from a severe craniocerebral trauma, respiration with a xenon-oxygen mixture, as also used in anesthesia, can prevent, or at least reduce, the release of dopamine and thus the secondary neurotoxic effects accompanying this trauma. In such accidents, the additional anesthetic side-effect is desired, since the patient can be freed from pain thereby.

An essential feature of acute ischemia in the brain is represented by the secondary neurotoxic effects which form by an increase in the neurotransmitter release, and are responsible for the death of the neurons in the ischemic marginal region. Although an immediate xenon treatment, e.g. by the emergency physician who carries out the initial treatment in the case of an apoplexy patient, cannot prevent ischemia per se, but it can at least reduce, or even prevent, the neurotoxicity by the secondarily released neurotransmitters. Thus, the permanent damage frequently occurring in the case of apoplexy can be reduced. The same applies analogously to measures which will have to be taken if disease symptoms occur after drug abuse and loss of hearing, or a migraine attack.

In the case of oxygen deficiency during a birth, e.g. during the entrance into the obstetric canal or in the case of problems with the umbilical cord, xenon-(oxygen) respiration of the mother and respiration of the child as soon after the birth as possible, respectively, can prevent the negative effects of increased dopamine release during the oxygen deficiency.

In the case of schizophrenia, patients suffer from periodic schizophrenia (catatonia), the progress is very sudden, the picture of the state being characterized by dramatic symptoms which show varying pictures and are full of delusions and hallucinations. Often a phase disappears as rapidly as it started. Such phases or attacks can be triggered spontaneously by stress situations. Rapid respiration with a xenon gas mixture during the state of stress can at least reduce the intensity of the attack. For this application, it is an obvious thing to equip patients with xenon inhalators which permit self-medication. In this case, it is conceivable to use containers which, similar to asthma sprays, are filled with xenon which will be released if a trigger is pressed. The same applies analogously to the treatment of depressive patients whose moods change almost daily and who as a result thereof require state-related medication.

Chronic Parkinson's disease is accompanied by progressive symptoms. A consequent xenon treatment reduces the neurotransmitter release and slows down the progression, or even brings the progression of the disease to a stand-still. In this case, intermittent treatment offers itself in which the patient is respirated with xenon at certain intervals. The same applies to patients who suffer from the Gilles de la Tourette syndrome. Their tics also become more and more distinct as the disease proceeds.

In the case of acute threatening states, such as a craniocerebral trauma or an ischemia, respiration can advantageously be carried out with a xenon-oxygen mixture of 90:10% by volume, preferably 80:20% by volume, and most preferably 75-70:25-30% by volume, over several hours to one day. As compared thereto, the intermittent respiration by a xenon-air mixture to which less xenon has been added, e.g. 5 to 30% xenon, preferably 10 to 20% xenon, can be considered in chronic progressions of a disease.

Various methods for the inhalation of xenon and xenon mixtures, respectively, can be used which depend on the respective intended use. In clinics, it is possible to use anesthetic apparatus, in which prefabricated xenon-oxygen mixtures can be connected to the corresponding inlets of the anesthetic apparatus. Respiration is then carried out according to a procedure which is common for such apparatus. The same applies analogously to the cardio-pulmonary bypass machine.

As an alternative, xenon can be mixed with ambient air instead of oxygen in the mobile use, which due to the smaller size of the required pressure bottles increases the mobility of the apparatus. For example, it is possible to use an inhalator which supplies xenon from a pressure bottle and is accommodated in a support, together with the latter, to a mixing chamber. On one side, this mixing chamber contains a mouthpiece for inhaling the xenon, and on the other side on which the xenon is supplied to the mixing chamber it has at least one additional check valve which enables the inlet of ambient air. The xenon pressure container can be equipped with a pressure reducing valve, for example, which reduces the amount of xenon gas supplied to a suitable value. When the patient breathes in, he sucks in air from the air valves. In the mixing chamber, this air is mixed with the supplied xenon to the desired ratio and then inhaled by the patient. An advantageous inhalator intended for mobile use and serving for inhaling xenon and its mixtures is shown in, for example, European Patent No. 560,928.

In a further simplified embodiment, e.g. for self-medication, a mouthpiece is connected directly to the xenon pressure container. During inhalation, the patient opens the pressure valve and inhales xenon simultaneously with the air from the environment. When he breathes out, he releases the valve, so that no more xenon reaches the mouthpiece. In this manner, at least a coarse regulation of the amount of inhaled xenon is possible.

Figure 1B:
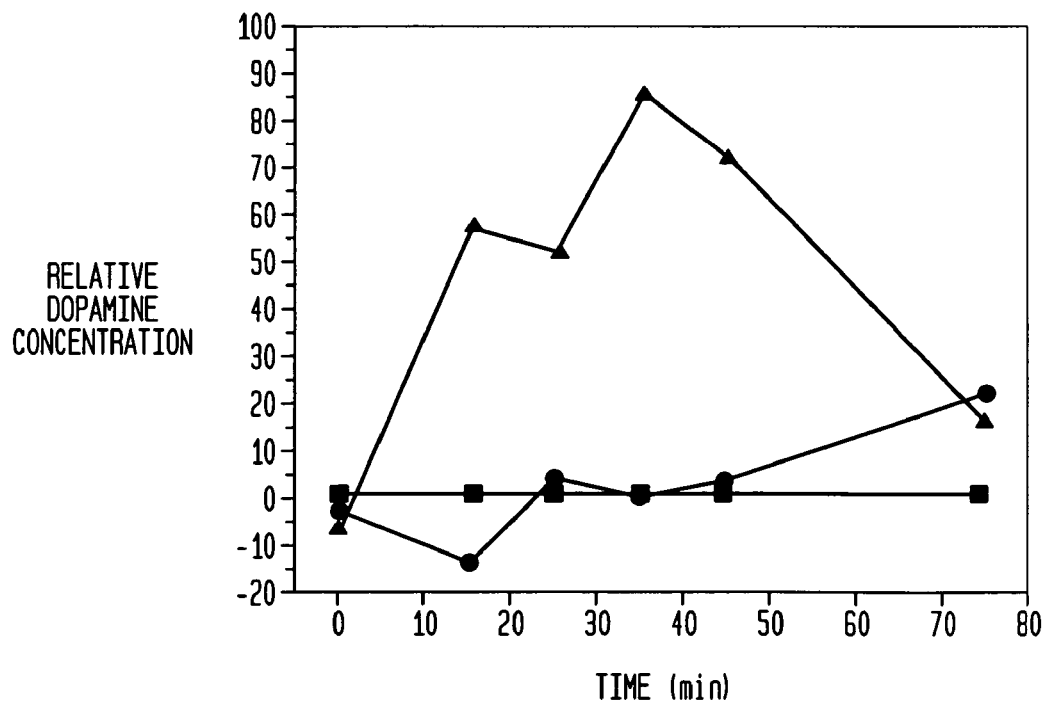
FIG. 1B is a graphical representation of relative dopamine concentration as a result of various hypoxic situations.

The present invention is explained in more detail below, reference being made to attached FIGS. 1 and 2, which show the dopamine release in cell cultures exposed to hypoxic shock.

The function of the present invention shall be explained in more detail below by means of the following examples.

Example 1

An in vitro experiment with PC12 cells is concerned. These PC12 cells are dependants of a pheochromocytoma of rats. Here a catecholamine-producing tumor of the suprarenal cortex is concerned, which shows permanent dopamine release in a malignant form. PC12 cells can be reproduced continuously in vitro. Following the addition of "nerve growth factor", they start differentiating and become neurons which in many respects have the property of in vivo neurons, particularly the properties which relate to the neurotransmitter release. PC12 cells are acknowledged as neuronal model.

PC12 cells differentiated in such a manner when exposed to a hypoxic situation, release dopamine. Such a hypoxic situation is an artificially induced stress state for the cells, in which e.g. the oxygen supply is dropped or impeded. If the cells are treated under these hypoxic conditions with xenon in defined concentrations over the same period of time, the neurotransmitter release will be dropped. The time course of such an experiment is shown in FIG. 1 by way of example. The curve of the non-stressed controls, illustrated by solid squares, shows a low dopamine concentration throughout the time course, which is subject to certain fluctuations. If a hypoxic situation is triggered by a dose of helium instead of oxygen, the curve of the dopamine concentration will result as shown in the curve produced from the solid triangles. A maximum dopamine concentration is shown in this case after about 40 minutes. However, if xenon is given in a hypoxic situation, the cells will virtually no longer differ from the control cell population, as shown by the plot illustrated by solid circles. In connection with the relative dopamine concentration shown in part B of FIG. 1 it can also be clearly seen that the dopamine release is reduced down to values of the control cells. In this connection, it was found that the xenon effect is fully reversible, so that the cells treated in this way cannot be distinguished from untreated cells after the xenon is washed out. In the above-described experiment, the gases used were given to the cells by mixing them with the growth buffer for the cells. In this case, saturated gas buffer solutions are involved.

Example 2

The differentiated PC12 cells described in Example 1 were distributed to various vessels and exposed to differing conditions. The results are shown in FIG. 2. These conditions are defined as follows:
Control: incubation in normal atmosphere (ambient air)
N2: incubation in nitrogen (N2) for 30 minutes [=hypoxia]
Xenon: incubation in xenon for 30 minutes
Glu: addition of 10 M glutamate for 30 minutes of incubation in a normal atmosphere
Glu+N2: addition of 10 M glutamate for 30 minutes of incubation in N2
Glu+Xe: addition of 10 M glutamate for 30 minutes of incubation in xenon.

A hypoxic condition and an increased release of dopamine resulted in the cells incubated with nitrogen (group: N2). The dopamine release may even be increased if, in addition to the nitrogen atmosphere, glutamate, which represents a neurotransmitter and has a neurotoxic effect in greater doses, was given as well (group: Glu+N2). However, if 10 M glutamate was given in the simultaneous presence of xenon (Group: Glu+Xe), a slightly increased dopamine release would still result, but which was nevertheless reduced by two-thirds as compared to the corresponding (glutamate+$N_2$) experiment.

Figure 2:
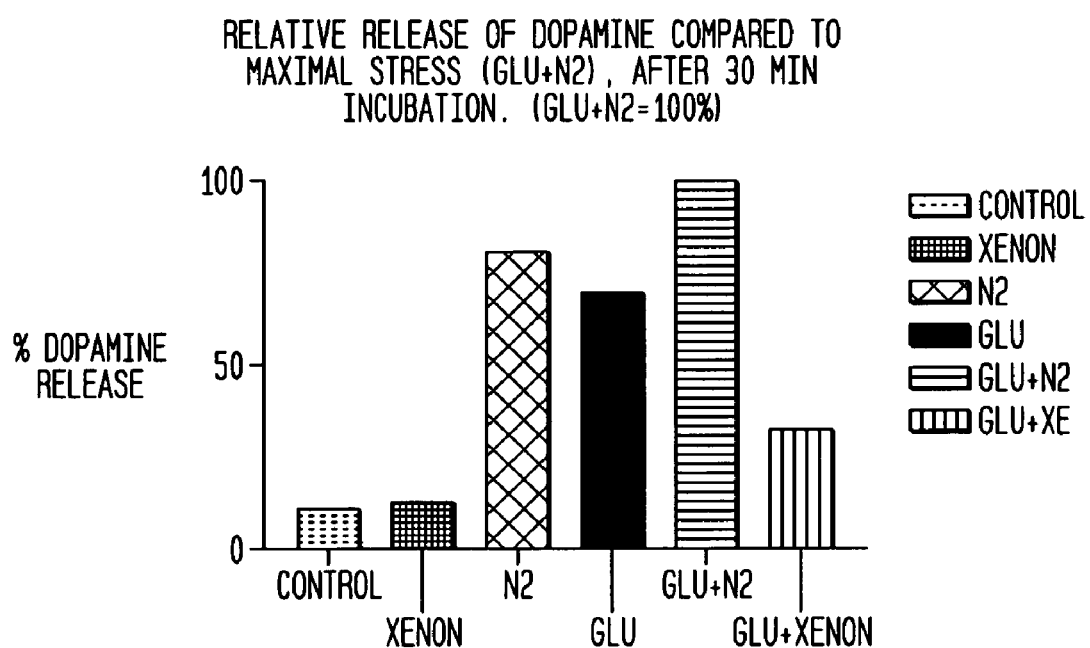
FIG. 2 is a graphical representation showing release of dopamine in various stress situations.

The results shown in FIG. 2 demonstrate that in stress situations such as hypoxia, the neurotransmitters glutamate and dopamine are released in large quantities. This results in a) direct damage to the neighboring neuronal tissues, mainly by inducing apoptosis and b) indirectly, an additional increased release of other neurotransmitters. Thus, the addition of glutamate to the cells effects an increased dopamine release, particularly when the cells are kept under hypoxic conditions. The unintentional neurotransmitter release could be reduced many times over by the simultaneous supply of xenon.

It can therefore be shown, on an overall basis, that in the present invention xenon can stop rapidly and without other permanent side-effects the neurotransmitter release temporarily. Hence it follows that xenon can be used in defined concentrations in a therapeutically useful manner in all pathologic conditions characterized by unregulated neurotransmitter release. The simple application by inhalation and the harmlessness of xenon render this therapy especially attractive. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of reducing neurotoxicity caused by increased release of neurotransmitters during ischemia comprising:
   administering to a mammal suffering from ischemia a therapeutically effective amount of xenon to reduce said neurotoxicity,
   wherein the xenon is administered as a 90:10 percent by volume xenon-oxygen mixture.

2. A method of reducing neurotoxicity caused by increased release of neurotransmitters during ischemia comprising:
   administering to a mammal suffering from ischemia a therapeutically effective amount of xenon to reduce said neurotoxicity,
   wherein the xenon is administered with ambient air.

3. A method of reducing neuron death caused by increased release of neurotransmitters during ischemia comprising:
   administering to a mammal suffering from ischemia a therapeutically effective amount of xenon to reduce the neuron death,
   wherein the xenon is administered with ambient air.

4. A method of treating a mammal suffering from ischemia by reducing neurotoxicity caused by increased release of neurotransmitters during the ischemia, the method comprising:
   administering to the mammal suffering from ischemia a therapeutically effective amount of xenon to reduce the neurotoxicity to treat the ischemia,
   wherein the xenon is administered with ambient air.

5. A method of treating a mammal suffering from ischemia by reducing neuron death caused by increased release of neurotransmitters during the ischemia comprising:
   administering to the mammal suffering from ischemia a therapeutically effective amount of xenon to reduce the neuron death to treat the ischemia,
   wherein the xenon is administered with ambient air.

6. A method of treating a mammal suffering from acute ischemia comprising:
   administering to the mammal suffering from acute ischemia a therapeutically effective amount of xenon to treat the acute ischemia,
   wherein the xenon is administered as a 90:10 percent by volume xenon-oxygen mixture.

7. A method of treating a mammal suffering from acute ischemia comprising:
   administering to the mammal suffering from acute ischemia a therapeutically effective amount of xenon to treat the acute ischemia,
   wherein the xenon is administered with ambient air.

8. A method of reducing neuron death caused by increased release of neurotransmitters during ischemia comprising:
   administering to a mammal suffering from ischemia a therapeutically effective amount of xenon to reduce the neuron death,
   wherein the xenon is administered over several hours to one day.

9. A method of treating a mammal suffering from ischemia by reducing neurotoxicity caused by increased release of neurotransmitters during the ischemia, the method comprising:
   administering to the mammal suffering from ischemia a therapeutically effective amount of xenon to reduce the neurotoxicity to treat the ischemia,
   wherein the xenon is administered over several hours to one day.

10. A method of treating a mammal suffering from ischemia by reducing neuron death caused by increased release of neurotransmitters during the ischemia comprising:
    administering to the mammal suffering from ischemia a therapeutically effective amount of xenon to reduce the neuron death to treat the ischemia,
    wherein the xenon is administered over several hours to one day.

11. A method of treating a mammal suffering from acute ischemia comprising:
    administering to the mammal suffering from acute ischemia a therapeutically effective amount of xenon to treat the acute ischemia,
    wherein the xenon is administered over several hours to one day.

* * * * *